(12) United States Patent
Huang (10) Patent No.: US 8,206,290 B2
(45) Date of Patent: Jun. 26, 2012

(54) MEDICAL INSPECTION DEVICE

(75) Inventor: Tzai-Kun Huang, Taipei (TW)

(73) Assignee: Apple Biomedical, Inc., Taipei (TW)

( * ) Notice: Subject to any disclaimer, the term of this patent is extended or adjusted under 35 U.S.C. 154(b) by 352 days.

(21) Appl. No.: 12/575,469

(22) Filed: Oct. 8, 2009

(65) Prior Publication Data

US 2011/0087073 A1 Apr. 14, 2011

(51) Int. Cl.
*A61B 1/227* (2006.01)
*A61B 1/06* (2006.01)

(52) U.S. Cl. ........................................ 600/200; 600/245

(58) Field of Classification Search .................. 600/200, 600/237–249, 109, 110, 131, 160, 172, 175, 600/476–480; 604/95.04, 164.01, 523–532, 604/95.01–95.05, 57–64; *A61B 1/227, 1/233*
See application file for complete search history.

(56) References Cited

U.S. PATENT DOCUMENTS

| | | | | |
|---|---|---|---|---|
| 6,106,457 | A * | 8/2000 | Perkins et al. | 600/175 |
| 2004/0140962 | A1* | 7/2004 | Wang et al. | 345/179 |
| 2005/0010084 | A1* | 1/2005 | Tsai | 600/200 |
| 2008/0204429 | A1* | 8/2008 | Silverbrook et al. | 345/179 |

* cited by examiner

*Primary Examiner* — Eduardo C Robert
*Assistant Examiner* — Jacqueline Johanas
(74) *Attorney, Agent, or Firm* — Hershkovitz & Associates LLC; Abraham Hershkowitz (57) ABSTRACT

An improved medical inspection device at least comprises a hand-held portion, a display portion being connected with the hand-held portion and comprising a first printing circuit board, an image display module, an annular protuberance and at least one electrode contact, an inspection module comprising a joint portion, an inspection portion and a third printing circuit board, wherein the joint portion has a second printing circuit board provided at an inner surface thereof, and the inspection portion further comprises a lens, an image sensing unit and a light source, and a fastening ring that is detachably fastened with the annular protuberance of the display portion so as to firmly fasten the joint portion of the inspection module to the display portion.

17 Claims, 10 Drawing Sheets

PRIOR ART

MEDICAL INSPECTION DEVICE

BACKGROUND OF THE INVENTION

1. Technical Field

The present invention related to a medical inspection device, and more particularly, to an improved medical inspection device including a hand-held portion, a display portion, and an inspection module.

2. Description of Related Art

It is common that doctors use conventional hand-held examining devices for otologic, peroral or nasal endoscopy to facilitate diagnosing their patients. Such a conventional hand-held examining device is configured like a magnifying glass, having a grip shank and an observing part. The observing part has its front end formed in a taper for easily entering an organ to be examined. At the distal portion of the tapered part, there is a lens for magnifying an image inside the interior of the organ to be examined so as to facilitate a doctor's diagnosis.

However, in use of the conventional hand-held examining device, to observe the magnified image, the user (i.e. the doctor) has to approach his/her eye to the observing part to look steadily at the lens. This can probably bring eyestrain to the user, and thus is not an ideal way to make observation. Besides, in use of the conventional hand-held examining device, additional light sources are usually required to illuminate the dark interior of organs for clear observation, thus forming another inconvenience. Moreover, after observation is made by using such a hand-held examining device, the only way to record the observed images is the doctor's sketches on paper. Consequently, the correctness of anamneses can be deteriorated if there is any inaccuracy existing in such sketches.

Figure 1:
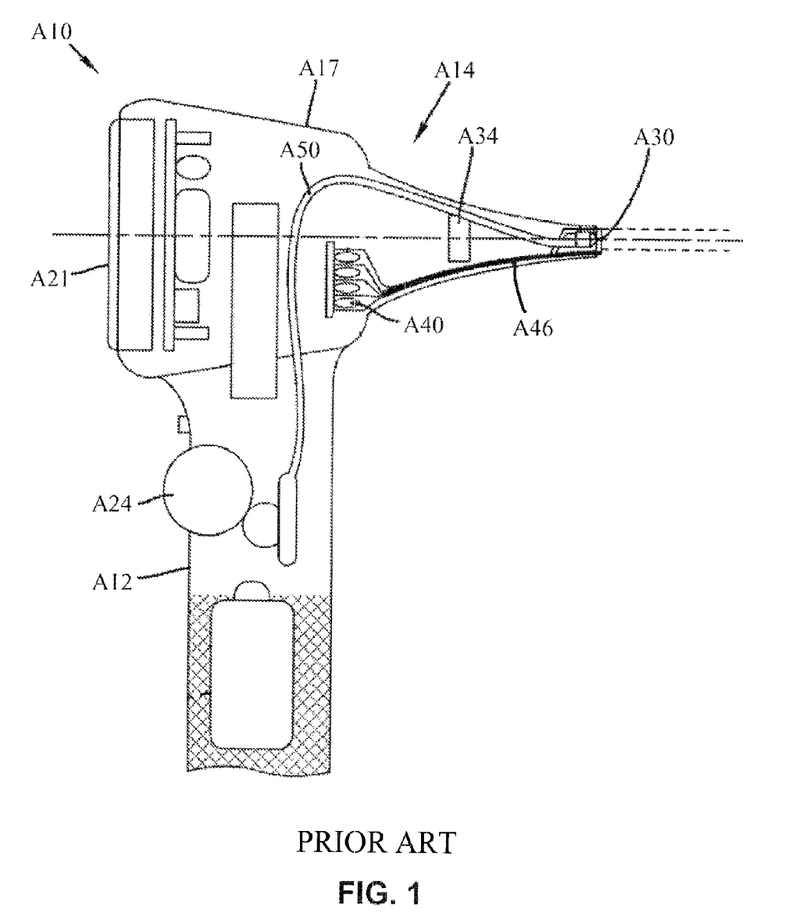
FIG. 1 is a sectional view of a conventional medical inspection device.

In view of this, there has been proposed a medical inspection device for remedying the shortcomings of the traditional hand-held examining devices. FIG. 1 is a sectional view of a conventional medical inspection device. The medical inspection device A10 includes a body A12 for a user to grip, a display portion A17 that has a screen A21, a speculum portion A14 that has a lens A30 at a front end thereof for entering an organ to be examined and capturing images, a sensor A34 converting the images into video signals; a focus control switch A24 for adjusting a focal length of the lens A30 through a cable A50, and a plurality of light generators A40, which are LEDs for emitting light beams that are then projected to an external target object through a light pipe A46 for illuminating the field of view. Therein, the body A12, the display portion A17, and the speculum portion A14 are enclosed by an integratedly formed housing and made not detachable.

After every single time of use, the speculum portion A14 directly contacting a patient's organ needs to be disinfected. However, since the medical inspection device A10 is integratedly formed, it is impossible to detach the speculum portion A14 for separate disinfection, thus being very inconvenient. In another case where any of the components inside the speculum portion A14 fails, replacement or repair of the problem component can never be accomplished unless the entire medical inspection device A10 is disassembled.

On the other hand, along the route defined by the light pipe A46 where the light emitted by the light generator A40 proceeds to the target object, the optical energy is more or less lost during the transmission along the light pipe A46. Besides, the light pipe A46 itself increases the overall manufacturing cost.

In view of this, it is necessary to provide an improved medical inspection device that addresses all the shortcomings of the prior art devices.

SUMMARY OF THE INVENTION

Hence, to remedy the problems and disadvantages of the prior art, the inventor of the present invention, relying on his years of experience, fully implemented his imagination and creativeness, to repeatedly experiment and make modification, and eventually developed an improved medical inspection device as claimed in the present application.

The primary objective of the present invention is to provide a medical inspection device, which has an inspection portion detachably assembled with its body, so as to allow more convenient repair and maintenance.

The secondary objective of the present invention is to provide a medical inspection device, which has a light source arranged at an end of its speculum portion, so as to save the use of any additional light pipe that is required in the prior art devices, thereby reducing the manufacturing cost.

Therefore, the present invention provides a medical inspection device, which at least includes a hand-held portion, allowing a user to hold and operate the medical inspection device; a display portion, fixedly coupled to one end of the hand-held portion, and further comprising at least: a first printed circuit board, arranged inside the display portion; an image display module, arranged on a surface of the display portion for displaying a particular image; an annular protuberance, arranged on another surface of the display portion opposite to the surface having the image display module; and at least one electrode contact, arranged on the surface of the display portion in an area circled by the annular protuberance, and electrically connected with the first printed circuit board; an inspection module, further comprising: a joint portion, arranged at one end of the inspection module, and having an inner surface provided with a second printed circuit board, the joint portion being engaged in a space bordered by the annular protuberance of the display portion so that the electrode contact contacts the second printed circuit board, causing the first printed circuit board and second printed circuit board electrically connected; an inspection portion, arranged at another end of the inspection module opposite to the end having the joint portion, and further comprising: a lens, arranged and exposed at the inspection portion, for taking an image of an external target object; an image sensing unit, arranged inside the inspection portion and connected with the lens, for receiving the image taken by the lens and converting the image into a video signal; and a light source, arranged inside the inspection portion adjacent to the lens, for emitting and projecting a light onto the target object so as to improve clearness of the taken image; a third printing printed circuit board, arranged inside the inspection module and connected between the image sensing unit and the second printed circuit board, the image sensing unit thus being able to transmit the video signal of the image to the image display module through the third printed circuit board, the second printed circuit board, and the first printed circuit board, and to display the image through the screen; and a fastening ring, detachably fastened to the annular protuberance of the display portion, so as to affix the joint portion of the inspection module firmly to the display portion.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENTS

To achieve the foregoing objectives and effects, the inventor of the present invention makes improvement to the conventional medical inspection device, by configuring the inspection portion as detachable, and rearranging the internal components, so as to excogitate an improved medical inspection device of the present invention. Hereinafter, a first preferred embodiment and a second preferred embodiment of the medical inspection device of the present invention will be described in detail so as to illustrate the structural and technical features of the present invention.

Figure 2:
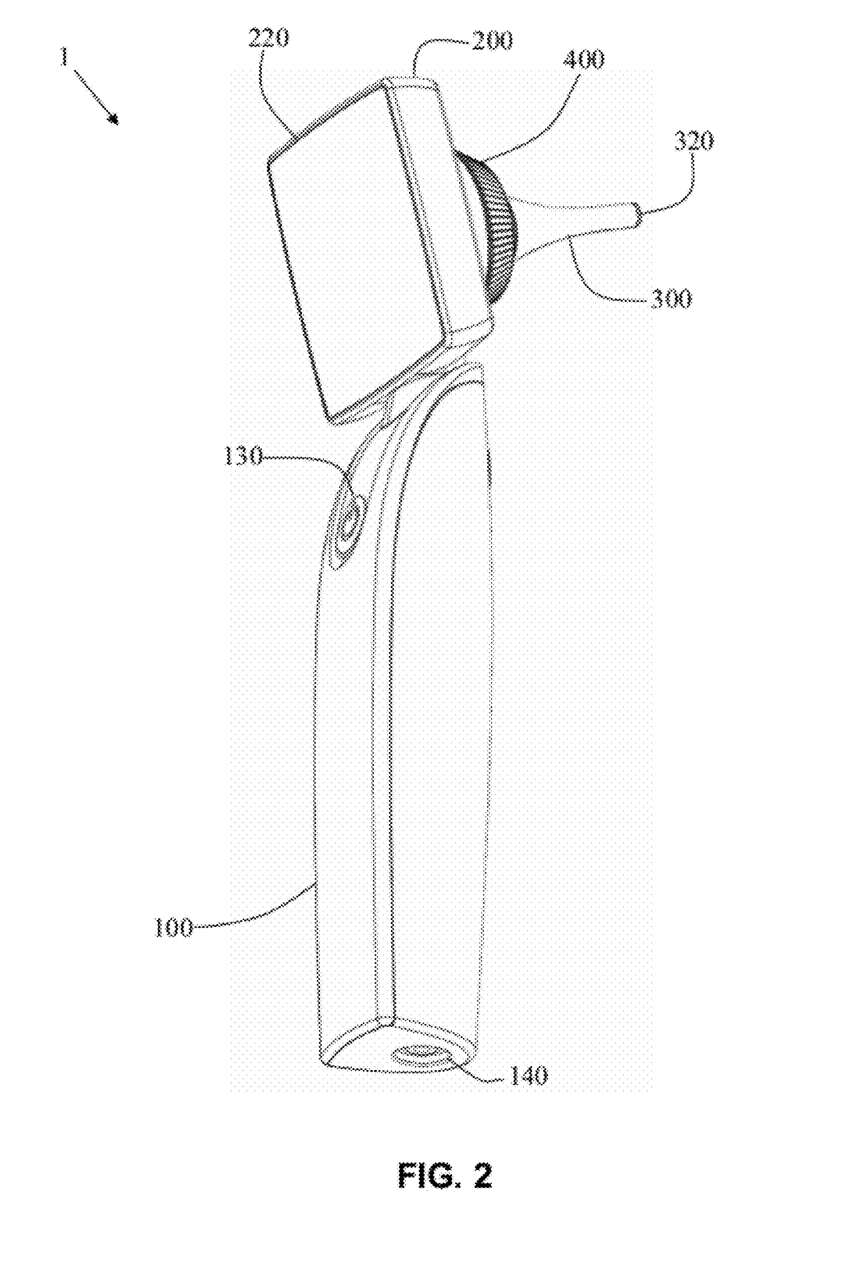
FIG. 2 is a perspective view of a medical inspection device according to a first preferred embodiment of the present invention.
Figure 3:
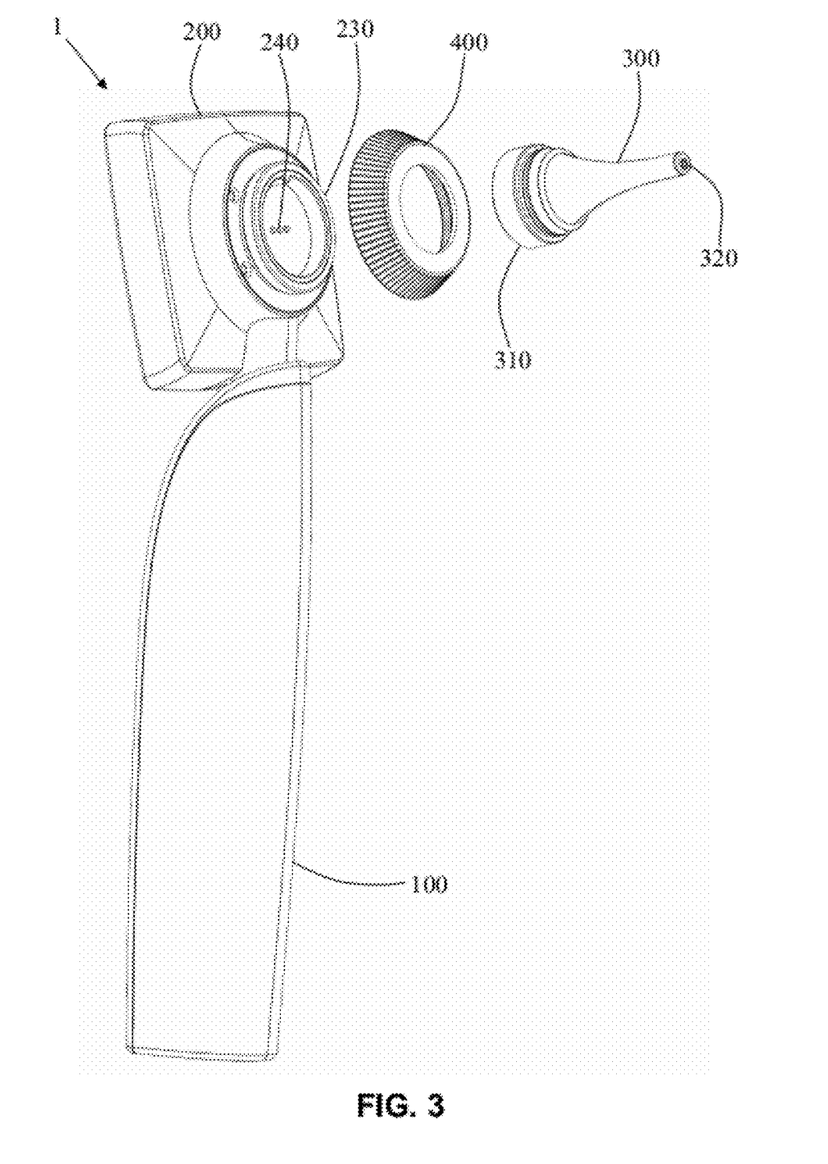
FIG. 3 is a partially exploded view of the medical inspection device according to the first preferred embodiment of the present invention.
Figure 4:
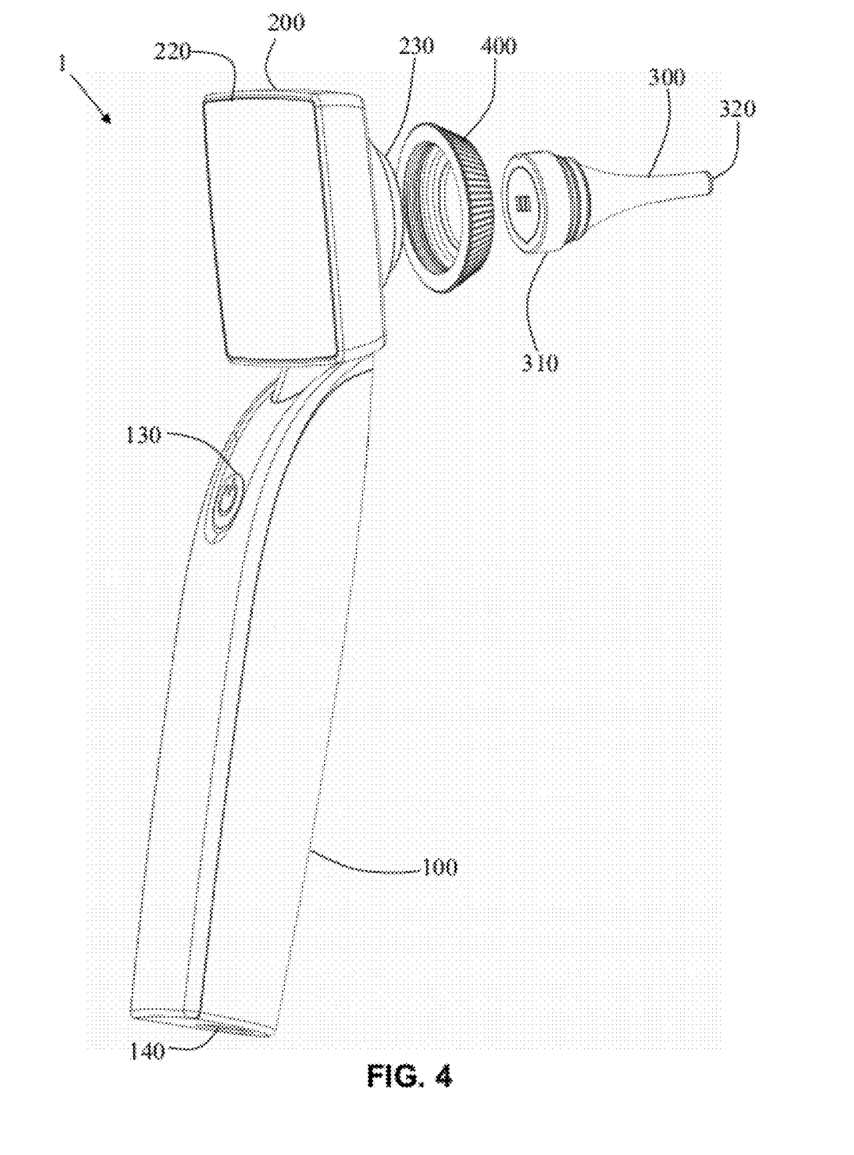
FIG. 4 is a partially exploded view of the medical inspection device according to the first preferred embodiment of the present invention taken from a different viewpoint.
Figure 5:
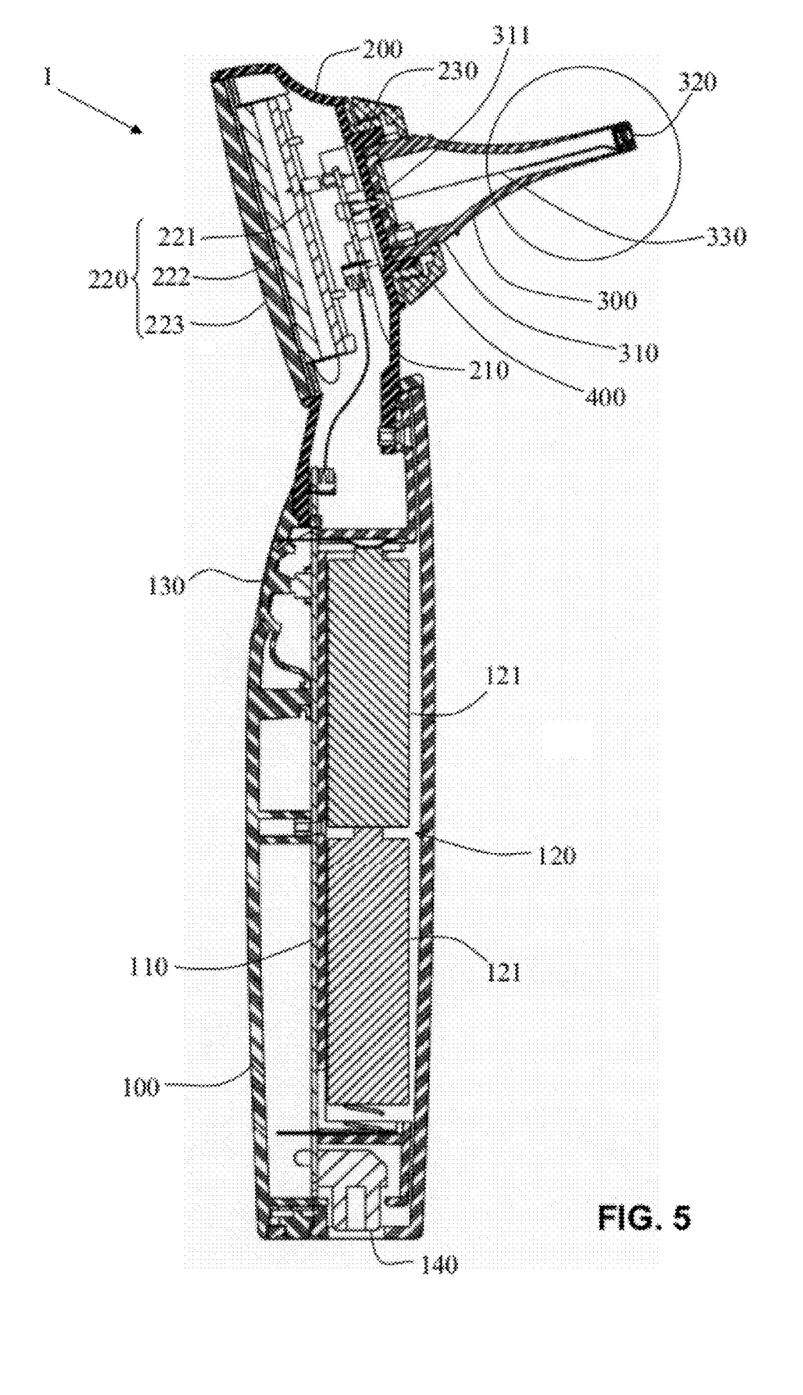
FIG. 5 is a sectional view of the medical inspection device according to the first preferred embodiment of the present invention.
Figure 6:
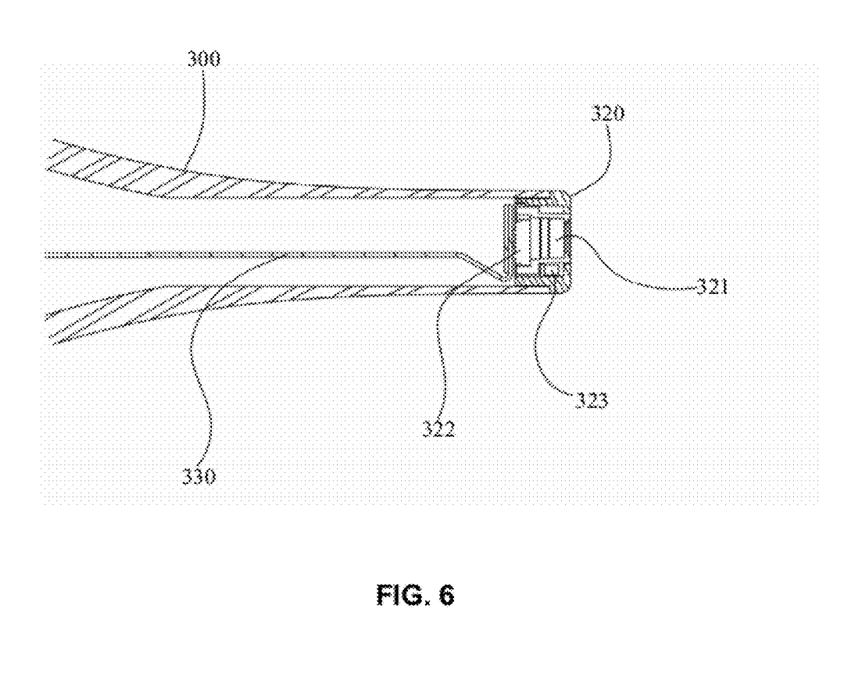
FIG. 6 is an enlarged drawing showing the circled area of FIG. 5.

Firstly, please refer to FIG. 2, FIG. 3, FIG. 4, FIG. 5 and FIG. 6 simultaneously. FIG. 2 is a perspective view of a medical inspection device according to a first preferred embodiment of the present invention. FIG. 3 is a partially exploded view of the medical inspection device according to the first preferred embodiment of the present invention. FIG. 4 is a partially exploded view of the medical inspection device according to the first preferred embodiment of the present invention taken from a different viewpoint. FIG. 5 is a sectional view of the medical inspection device according to the first preferred embodiment of the present invention. FIG. 6 is an enlarged drawing showing the circled area of FIG. 5. As shown in the drawings, the medical inspection device 1 according to the first preferred embodiment of the present invention primarily comprises a hand-held portion 100, a display portion 200, an inspection module 300, and a fastening ring 400.

The hand-held portion 100 is provided for a user to grip, thereby facilitating the user's operation of the medical inspection device 1.

The display portion 200 is fixedly coupled with one end of the hand-held portion 100. The display portion 200 further comprises a first printed circuit board 210 arranged inside the display portion 200, and an image display module 220 arranged on a surface of the display portion 200 for displaying a particular image. The image display module 220 is composed of a fourth printed circuit board 221, a screen 222, and a transparent protective cover 223. The fourth printed circuit board 221 is electrically connected with the first printed circuit board 210 for transmitting power and signals. The screen 222 abuts on a surface of the fourth printed circuit board 221 opposite to a surface of the fourth printed circuit board 221 connected with the first printed circuit board 210. The transparent protective cover 223 abuts on a surface of the screen 222 opposite to a surface of the screen 222 abutting on the fourth printed circuit board 221. Therein, the screen 222 is a liquid crystal display (LCD). An annular protuberance 230 is arranged on the surface of the display portion 200 opposite to the surface of the display portion 200 having the image display module 220. In addition, a plurality of electrode contacts 240 is arranged on the surface of the display portion 200 in an area circled by the annular protuberance 230 and are electrically connected with the first printed circuit board 210.

The inspection module 300 further comprises a joint portion 310 arranged at one end of the inspection module 300. The joint portion 310 has a second printed circuit board 311 arranged on its inner surface. The joint portion 310 is designed to be fittingly engaged in a space bordered by the annular protuberance 230 of the display portion 200. The plural electrode contacts 240 are configured to contact the second printed circuit board 311 so as to cause the first printed circuit board 210 and the second printed circuit board 311 to be electrically connected with each other. An inspection portion 320 is arranged at another end of the inspection module 300 opposite to the end of the inspection module 300 having the joint portion 310, and comprises a lens 321, an image sensing unit 322, and a light source 323. The lens 321 is arranged and exposed at the inspection portion 320 for taking an image of an external target object. The image sensing unit 322 is arranged inside the inspection portion 320 and connected with the lens 321 for receiving the image taken by the lens 321 and converting the image into a video signal. The light source 323 is arranged inside the inspection portion 320 and adjacent to the lens 321, and serves to emit and project a light onto the target object for improving clearness of the taken image. Therein, the light source 323 is a light emitting diode (LED). However, in practice, the light source may alternatively be a miniature incandescent bulb, a compact fluorescent light (CFL) or a laser device. A third printed circuit board 330 is arranged inside the inspection module 300 and connected between the image sensing unit 322 and the second printed circuit board 311. The image sensing unit 322 thus is able to transmit the video signal of the image to the image display module 220 by way of the third printed circuit board 330, the second printed circuit board 311, and the first printed circuit board 210, and to display the image through the screen 222. Therein, the third printed circuit board 330 is a flexible printed circuit (FPC).

The fastening ring 400 may be detachably coupled to the annular protuberance 230 of the display portion 200, so as to make the joint portion 310 of the inspection module 300 firmly coupled to the display portion 200.

In the foregoing first preferred embodiment, matched threads are further provided at an outer periphery of the annular protuberance 230 and an inner periphery of the fastening ring 400, respectively, so that by the screwedly combined threaded peripheries, the annular protuberance 230 and the fastening ring 400 can be firmly fastened together. However, in practical application, the annular protuberance 230 and the fastening ring 400 may be alternatively fastened by means of wedging or other screw fasteners. Moreover, the display portion 200 may be directly assembled with the inspection module 300 by means of wedging, without using the fastening ring 400.

Furthermore, in the first preferred embodiment, the hand-held portion 100 has additional components described below. A fifth printed circuit board 110 is arranged inside the hand-held portion 100 and is electrically connected with the first printed circuit board 210 in the display portion 200 for controlling power and transmitting video signals. An accommodating space 120 serves to accommodate two batteries 121. The two batteries 121 are electrically connected with the fifth printed circuit board 110 for providing power required by the medical inspection device 1. A power button switch 130 is electrically connected with the fifth printed circuit board 110 for turning on or off the power supply. An image transmission port 140 is electrically connected with the fifth printed circuit board 110 for transmitting the image taken by the lens 321 to an external device through a transmission line.

In the first preferred embodiment of the present invention, in addition to the image transmission port 140, a radio frequency (RF) module (not shown) may be further provided so as to transmit image data wirelessly to an external device through radio frequency. The RF module may be optionally arranged inside the hand-held portion 100 or the display portion 200.

Figure 7:
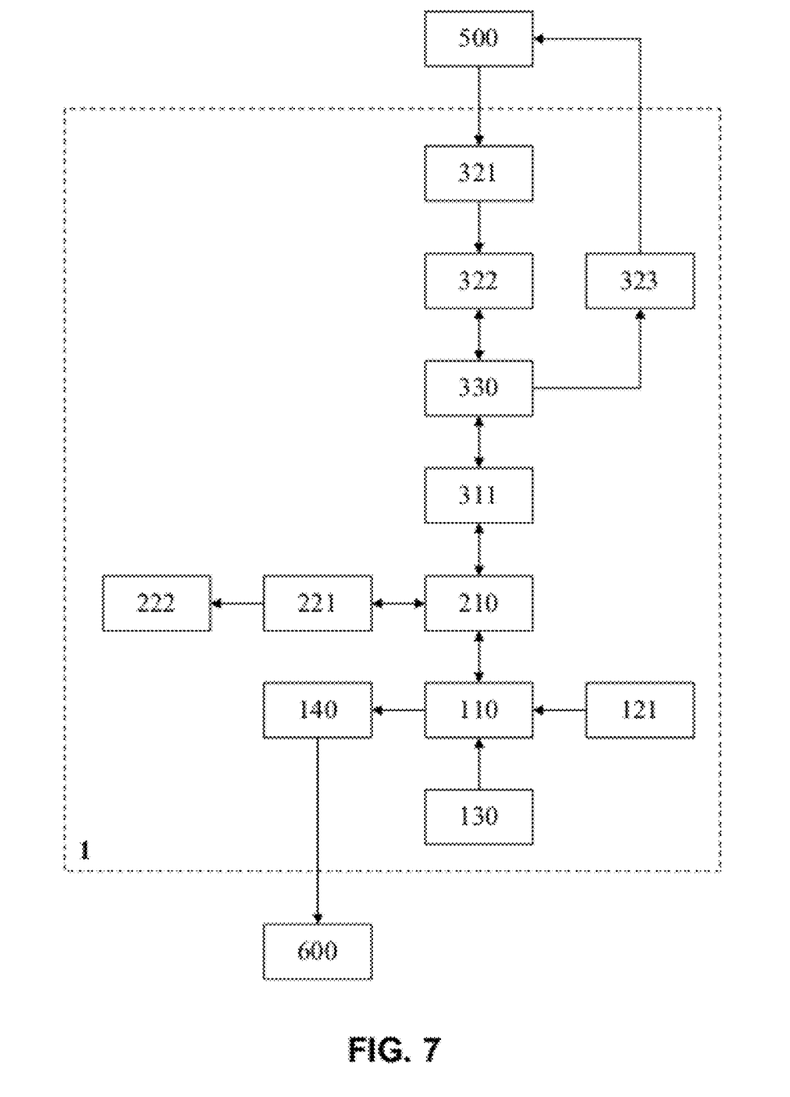
FIG. 7 is a schematic diagram illustrating electrical transmission among partial components of the medical inspection device according to the first preferred embodiment of the present invention.

Please refer to FIG. 7 for a schematic diagram illustrating electrical transmission among partial components of the medical inspection device according to the first preferred embodiment of the present invention. As can be seen in the diagram, the improved medical inspection device 1 is powered by the batteries 121. The power supply is transmitted to the second printed circuit board 311, the third printed circuit board 330, and the fourth printed circuit board 221 through the fifth printed circuit board 110 and the first printed circuit board 210, respectively. Then the third printed circuit board 330 delivers the power to the image sensing unit 322, the lens 321 and the light source 323 for their use while the fourth printed circuit board 221 delivers the power to the screen 222 for its use. Furthermore, the light source 323 projects the light onto a target object 500, and the lens 321 captures an image of the target object 500. Afterward, the image is converted into a video signal by the image sensing unit 322. The video signal may be subsequently transmitted to the screen 222 for display or transmitted to the image transmission port 140 so as to be further transmitted to an external device 600 through a transmission line. In addition, the power button switch 130 may be operated to turn on or off the power supply through the fifth printed circuit board 110.

Figure 8:
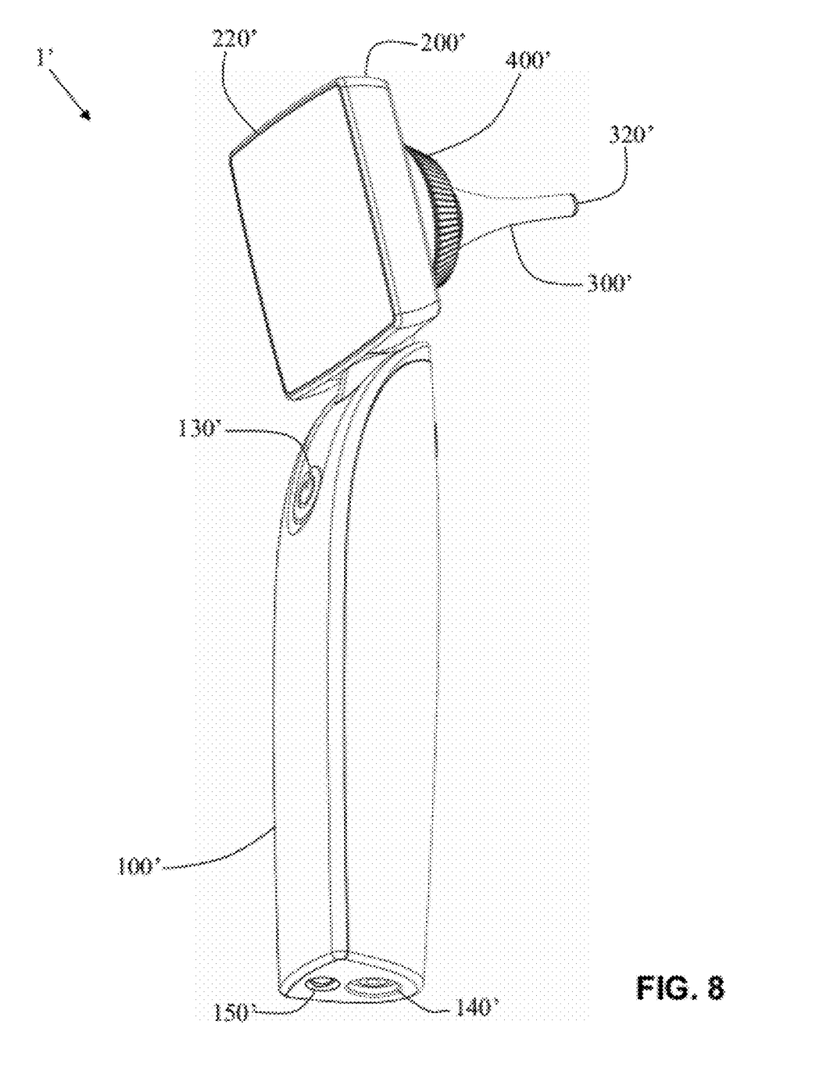
FIG. 8 is a perspective view of a medical inspection device according to a second preferred embodiment of the present invention.
Figure 9:
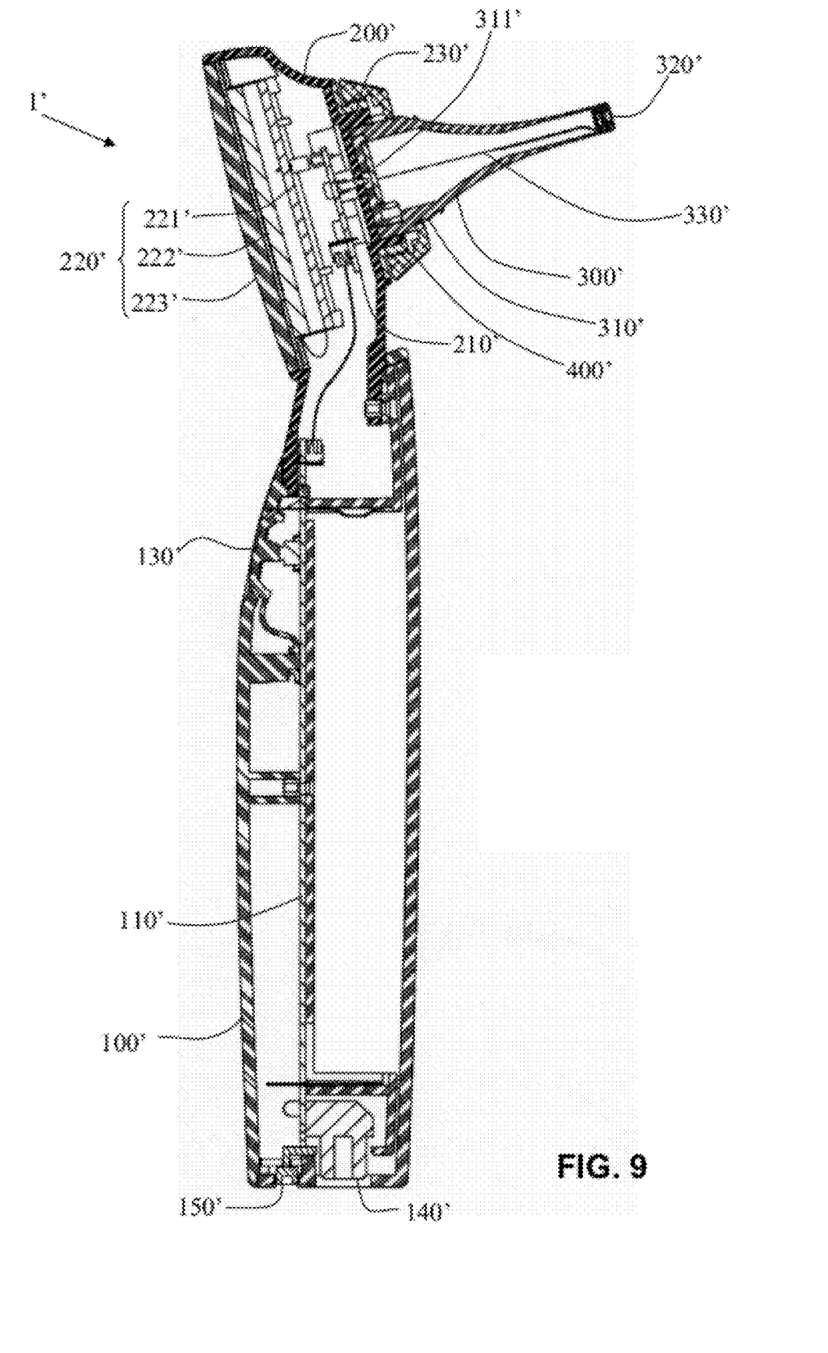
FIG. 9 is a sectional view of the medical inspection device according to the second preferred embodiment of the present invention.
Figure 10:
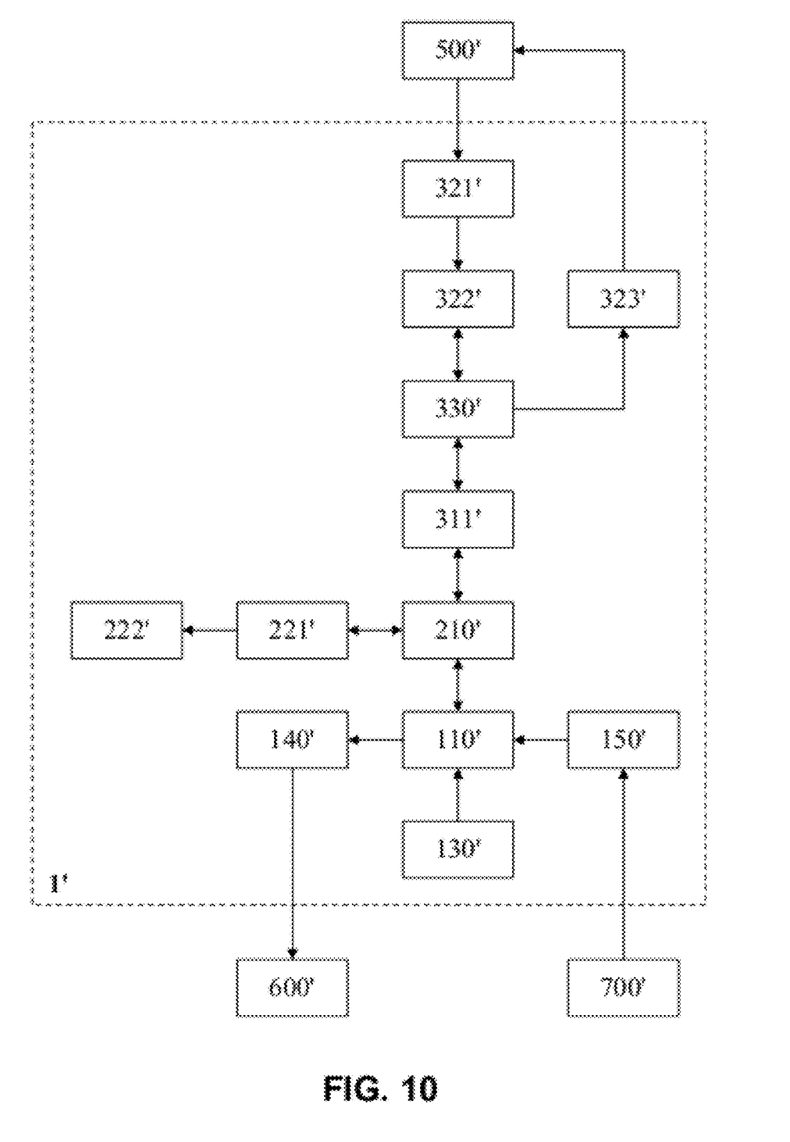
FIG. 10 is a schematic diagram illustrating electrical transmission among partial components of the medical inspection device according to the second preferred embodiment of the present invention.

Now please refer to FIG. 8, FIG. 9 and FIG. 10. FIG. 8 is a perspective view of a medical inspection device according to a second preferred embodiment of the present invention. FIG. 9 is a sectional view of the medical inspection device according to the second preferred embodiment of the present invention. FIG. 10 is a schematic diagram illustrating electrical transmission among partial components of the medical inspection device according to the second preferred embodiment. While the second preferred embodiment has most components in common with those of the first preferred embodiment, the details of these previously described components are omitted herein. The difference between the two embodiments lies in that, in a medical inspection device 1' according to the second preferred embodiment, a hand-held portion 100' has a power port 150', which is electrically connected with a fifth printed circuit board 110' arranged inside the hand-held portion 100'. The power port 150' is designed to connect an external power source 700', which provides power required by the medical inspection device 1'.

Through the above detailed illustration of the overall structural and technical features of the present invention, it can be summarized that the present invention has the following advantages:

1. The inspection module of the present invention is detachably assembled with the display portion, so that when the inspection module fails, when an inspection module with different functions is needed, or when the inspection module has to be disinfected independently, the currently assembled inspection module can be easily detached for repair, replacement or disinfection, thereby making the medical inspection device more convenient in its uses and maintenance.
2. The present invention uses the fastening ring to fasten the inspection module firmly to the display portion, so as to prevent the inspection module from coming off the display portion, thus improving structural stability in use.
3. In the present invention, the light source is directly arranged at the end of the inspection portion of the inspection module, so as to give immediate illumination to the target object in inspection and save the use of any light pipe that is required in the prior art devices, thus reducing the manufacturing cost.
4. The present invention converts the image of the target object into the video signal by using the image sensing unit, and displays the image through the screen, thereby allowing easy observation of the image.

What is claimed is:
1. A medical inspection device, comprising:
a hand-held portion, allowing a user to hold and operate the medical inspection device;
a display portion, fixedly coupled to one end of the hand-held portion, and further comprising at least:
a first printed circuit board, arranged inside the display portion;
an image display module, arranged on a surface of the display portion for displaying a particular image;
an annular protuberance, arranged on another surface of the display portion opposite to the surface having the image display module; and
at least one electrode contact, arranged on the surface of the display portion in an area circled by the annular protuberance, and electrically connected with the first printed circuit board;
an inspection module, further comprising:
a joint portion, arranged at one end of the inspection module, and having an inner surface provided with a second printed circuit board, the joint portion being engaged in a space bordered by the annular protuberance of the display portion so that the at least one electrode contact contacts the second printed circuit board, causing the first printed circuit board and second printed circuit board to be electrically connected;
an inspection portion, arranged at another end of the inspection module opposite to the end having the joint portion, and further comprising:
a lens, arranged and exposed at the inspection portion, for taking an image of an external target object;
an image sensing unit, arranged inside the inspection portion and connected with the lens, for receiving the image taken by the lens and converting the image into a video signal; and a light source, arranged inside the inspection portion adjacent to the lens, for emitting and projecting a light onto the target object so as to improve clearness of the taken image;

a third printed circuit board, arranged inside the inspection module and connected between the image sensing unit and the second printed circuit board, the image sensing unit thus being able to transmit the video signal of the image to the image display module through the third printed circuit board, the second printed circuit board, and the first printed circuit board, and to display the image through a screen; and a fastening ring, detachably fastened to the annular protuberance of the display portion, so as to affix the joint portion of the inspection module firmly to the display portion.

2. The medical inspection device of claim 1, wherein the image display module comprises a fourth printed circuit board, a screen, and a transparent protective cover, the fourth printed circuit board being electrically connected with the first printed circuit board for transmitting power and signals, and the screen abutting on a surface of the fourth printed circuit board opposite to a surface of the fourth printed circuit board connected with the first printed circuit board, while the transparent protective cover abutting on a surface of the screen opposite to a surface of the screen abutting on the fourth printed circuit board.

3. The medical inspection device of claim 2, wherein the screen is a liquid crystal display (LCD).

4. The medical inspection device of claim 1, wherein matched threads are further provided at an outer periphery of the annular protuberance and an inner periphery of the fastening ring, respectively, so that by the screw-combined threaded peripheries, the annular protuberance and the fastening ring are firmly fastened together.

5. The medical inspection device of claim 1, wherein the annular protuberance and the fastening ring are fastened together by wedging.

6. The medical inspection device of claim 1, wherein the annular protuberance and the fastening ring are fastened together by screw fasteners.

7. The medical inspection device of claim 1, wherein the light source is selected from the group consisting of a light emitting diode (LED), a miniature incandescent bulb, a compact fluorescent light (CFL), and a laser device.

8. The medical inspection device of claim 1, wherein the third printed circuit board is a flexible printed circuit (FPC).

9. The medical inspection device of claim 1, wherein the hand-held portion includes therein a fifth printed circuit board that is electrically connected with the first printed circuit board in the display portion for transmitting power and data.

10. The medical inspection device of claim 9, wherein the hand-held portion further has an accommodating space for accommodating at least a battery that is electrically connected with the fifth printed circuit board for providing power required by the medical inspection device.

11. The medical inspection device of claim 9, wherein the hand-held portion further has a power port that is electrically connected with the fifth printed circuit board, the power port being connected with an external power source for providing power required by the medical inspection device.

12. The medical inspection device of claim 9, wherein the hand-held portion further has a power button switch that is electrically connected with the fifth printed circuit board for turning on or off the power.

13. The medical inspection device of claim 9, wherein the hand-held portion further has an image transmission port that is electrically connected with the fifth printed circuit board for transmitting the image taken by the lens to an external device through a transmission line.

14. The medical inspection device of claim 1, wherein the medical inspection device further has a radio frequency (RF) module for wirelessly transmitting the image data to an external device through radio frequency.

15. The medical inspection device of claim 14, wherein the RF module is selectively arranged inside the hand-held portion and inside the display portion.

16. The medical inspection device of claim 1, wherein the inspection module is replaceable with alternative inspection modules having various configurations and appearances for examining different organs.

17. The medical inspection device of claim 1, wherein the image sensing unit is selected from the group consisting of a complementary metal oxide semiconductor (CMOS), a charge coupled device (CCD), and an image system-on-a-chip (image SOC).

* * * * *